(12) United States Patent
Cornel

(10) Patent No.: US 7,749,154 B2
(45) Date of Patent: Jul. 6, 2010

(54) SYSTEM AND METHOD FOR MANIPULATING SLEEP ARCHITECTURE BY SUB-AWAKENING NON-INTRUSIVE STIMULATIONS

(76) Inventor: Lustig Cornel, 5(A) Har Hazofim St., Rehovot (IL) 76620

( * ) Notice: Subject to any disclaimer, the term of this patent is extended or adjusted under 35 U.S.C. 154(b) by 1265 days.

(21) Appl. No.: 11/210,835

(22) Filed: Aug. 25, 2005

(65) Prior Publication Data
US 2005/0283039 A1 Dec. 22, 2005

Related U.S. Application Data

(63) Continuation-in-part of application No. PCT/IL2004/000187, filed on Feb. 25, 2004.

(51) Int. Cl.
*A61M 21/00* (2006.01)
(52) U.S. Cl. ........................................................ 600/27
(58) Field of Classification Search ............ 600/26–28, 600/544–546; 128/905
See application file for complete search history.

(56) References Cited

U.S. PATENT DOCUMENTS

| | | | |
|---|---|---|---|
| 3,884,218 A | 5/1975 | Monroe | 128/1 C |
| 5,163,426 A | 11/1992 | Czeisler et al. | 607/88 |
| 5,613,498 A | 3/1997 | Yasushi et al. | 128/731 |
| 7,041,049 B1 * | 5/2006 | Raniere | 600/26 |

OTHER PUBLICATIONS

Written Opinion for PCT/IL04/00187.
International Search Report for PCT/IL04/00187.
International Prelim Report on Patentability for PCT/IL04/00187.

* cited by examiner

*Primary Examiner*—John P Lacyk
(74) *Attorney, Agent, or Firm*—Martin Fleit; Paul D. Bianco; Fleit Gibbons Gutman Bongini & Bianco PL

(57) ABSTRACT

The present invention which is a new system and method employing stimulation control to treat sleep disorders, and improve sleep states operates in a dynamic, adaptable manner without causing a premature state of arousal. Stimulation is achieved by controlling a wide variety of environmental factors around the sleeping person. The invention is based on a real-time, self-adaptive feedback system including a sleep and environment monitoring unit or a preset adjustable protocol, an integrating, controlling and deciding unit and a stimulation unit. The system and method take into account individual variability and sensitivity to sensory stimulation and phenomena as adaptation and sensitization. The system and method are aimed at improving the overall sleep architecture, and correcting specific disorders. Alternatively the same invention may be used to promote alertness, specific moods and conditions in the awake subject. The invention may be used by professional in sleep laboratories or by individuals in a home environment. It may be adjusted to operate on groups of people and on non-human subjects.

34 Claims, 2 Drawing Sheets

SYSTEM AND METHOD FOR MANIPULATING SLEEP ARCHITECTURE BY SUB-AWAKENING NON-INTRUSIVE STIMULATIONS

This application is a continuation in part, claiming priority from PCT application no. PCT/IL/04/00187 filed on Feb. 25, 2004 having a priority date of Feb. 28, 2003. This invention relates to the field of sleep disorders and more particularly to methods for treating sleep disorders.

FIELD OF THE INVENTION

Background

Sleep medicine is a fast emerging independent branch of medicine. Many sleep disorders have been already characterized and others are in the process of characterization. Moreover in addition to the primary sleep disorders, sleep is affected by other conditions. These conditions cause secondary sleep disorders, in which sleep is affected by the primary cause. However because of the importance of sleep for physical, mental, cognitive, emotional, wellbeing, even in a secondary sleep disorder, improving sleep means improving person's condition and directly or indirectly improving the cause of the disorder.

As the western world encounters more and more sleep related difficulties (not enough sleep time, night shift working, stress, jet lag etc.), improving the quality of sleep (defined in a quantitative or qualitative manner) is one of the most promising steps towards improving the quality of life.

Measuring the quantitative aspect of sleep is determined via the monitoring of a wide range of physiological parameters such as melatonin levels, limbic movement, eye movement, central electroencephalography (EEG) (alpha, beta, delta and theta brainwaves), body temperature, muscle tonus, respiration patterns and intake, endocrine function and others. Sleep stages scoring and analysis are done by integrating some of these parameters according to established criteria and methods. The monitoring is performed in various degrees of automation, while the present day tendency is toward automated monitoring and automated processes of analysis, data integration and evaluation. The assessment of quality of sleep usually relays on tools such as questionnaires and interviews.

Treatment of sleep disorders is wide in purpose and scope; however, it can be divided into a few categories: medication, for example benzodiazepines or melatonin; psychological treatments, for example in the case of sleep disorders related to Post Traumatic Stress Disorder (PTSD); assisting devices during sleep, for example nasal CPAP (continuous positive airway pressure) for treating Obstructive Sleep Apnea Syndrome (OSAS); assisting devices during wake time, as for example 2500-10000 Lux fluorescent lightening system for treating hypersomnia or delayed sleep phase in SAD (seasonal affective disorder) patients; sleep hygiene—adopting new life habits, such as making changes in nutrition and eating habits, physical exercise and improving the sleep environment.

Previous patents have suggested the use of light, sound and temperature for regulating sleep: U.S. Pat. No. 5,163,426 for assessing and modifying the endogenous circadian cycle in an awaken subject applying alternately bright light and periods of darkness. European patent WO01/03751 describes an extra-ocular apparatus that exposes the subject to timed episodes of light in order to enhance rapid eye movement (REM) sleep. The purpose of the invention is to improve cognitive functions in the waking state by affecting the sleep.

European patent 469,227, describes a device that affects sleep by using "white" light. This patent incorporates sound and creating a magnetic field in order to not only effect the existing state of sleep but also to induce the sleep itself. This device operates on pre-set protocols and responds only upon unexpected awakening of the user.

U.S. Pat. No. 3,884,218 from 1975 discloses a system which produces a pleasant sound that induces sleep, maintains sleep and upon cessation of the sound the person wakes up. According to this patent the system compensates for ambient noise. However, the proposed system does not include a feedback system and the person's physiological state is not monitored. The appliance only enables controlling the volume of the sound and turning it on and off.

U.S. Pat. No. 5,613,498 describes an apparatus and a method for inducing a desired state in awake and in sleep. The apparatus is comprised of a sensor for detecting physiological data of a human body, a memory for storing the detected physiological data such as brain waves, skin temperature, and the like. A controller reads out the physiological data from the memory and supplies this data to a light modulator. The apparatus emits light and sound for the purpose of inducing the desired mental state in accordance with the physiological data.

However, the invention as disclosed in U.S. Pat. No. 5,613,498 has several shortcomings. The apparatus is designed to induce a particular mental state but it does not regard the complex dynamic of the human sleep and awake states, dynamics that need a continuous feedback and stimulation adjusting mechanisms. The apparatus is set to stop operating as the desired state is reached. Moreover, the invention disregards sleep events such as respiratory related events e.g. apnea, hypopnea and snoring and is not designed to handle such events. In addition, the disclosed apparatus is designed to only integrate particular data and disregards global considerations such as the number of session and duration of the subject's REM sleep stages. Its memory component is therefore only used to account for personal variability.

The main objective of the present invention is to improve the different stages of sleep, prevent non-desirable sleep events, and improve wakefulness time by employing gentle, sub-awakening sensory stimulations and other environmental conditions (i.e. temperature, magnetic field, etc.). Furthermore, the present invention provides a system and method that collects data about the state of the patient and of the sleeping environment, and adjusts the stimulation protocols in real time, in order to achieve specific predetermined targets. Further details and embodiments of the invention are discussed below.

SUMMARY

The present invention describes a system and a method for dynamically manipulating the sleep architecture toward treating sleep disorders, such as apnea, hypopnea, snoring, and improving sleep quality and the state of alertness and pattern behavior of a subject, said system and method comprising: sensory stimulation generators, monitoring means for measuring subject's physiological conditions and the environmental conditions. The sensory stimulation activation is based upon an interactive session algorithm, said algorithm include state analyzing module for analyzing user's state of alertness or phase therein according to sampled measurement of the subject physiological conditions, and convergence algorithms for determining the stimulation activation parameters accordingly. The algorithms have local and global convergence components.

Said system and method may alter the state of alertness and patterns of behavior related to sleep phases and sleep architecture and to awake phases and levels of activity such as sleepiness, drowsing driving and narcolepsy. The said sensory stimulation generators may generate and control light, sound, odor, temperature and mechanical stimulations. The convergence module operation is based on stimulation protocols relating to specific conditions for achieving specific targets, wherein the said protocols can be configured and adapted to the respective stimulation equipment. The stimulation protocols are based on translation module between sensory stimulation and expected effects in which the said algorithms can be configured and adapted to particular sensitivities and limitations.

Said system and method further comprising references profiles of disordered and or normal subjects wherein said references are used for analyzing subjects' condition and state for determining stimuli activation. This system and method may apply to humans, animals or plants in the air or in a fluid environment as well as for a single subject or for a conglomeration of subjects.

The said algorithm bases its decisions upon previous data measurements at earlier phases, the state analyzing module further analyses user state and current measurements to estimate next state of alertness. The data can be gathered via different channel specifications. The said system and method also include an analyzing means for processing historical data of the same subject and data from similar templates for improving the algorithm stimulation protocols.

BRIEF DESCRIPTION OF THE DRAWINGS

These and further features and advantages of the invention will become more clearly understood in the light of the ensuing description of a few preferred embodiments thereof, given by way of example only, with reference to the accompanying drawings, wherein.

DETAILED DESCRIPTION OF PREFERRED EMBODIMENTS

The disclosed invention promotes a new treatment approach based on affecting the sleep architecture in soft real time, by manipulating the users' sensory environment and other environmental conditions while they are asleep. The approach is directed toward specific predefined aims concerning the different stages of sleep and alertness. The present invention suggests using the system as a means for treating or improving specific known sleeping disorders, and for regulating and improving the sleep patterns (sleep architecture) of individuals who are not diagnosed as suffering from sleep disorders. The system and method are aimed for increasing the sleep quality and efficiency in a subject, as measured and scored quantitatively during sleep, upon awakening, and during waking hours, for short, medium, and long periods of time. The preferred embodiments of the present invention make use of one or more stimulation in the subjects' environment to create the desirable effect in their sleep architecture by effecting automatic, voluntary or cognitive mechanisms. Although the invention may operate on a single stimulation pathway, integrating more then one pathway in a coordinated manner has the potential of more efficient results, in particularly if the synaesthesia, adaptation and sensitization mechanisms and individual variability, ranging from preference, habits, adaptation, sensitization sensitivity to sensory perception limitation are taken into account.

In the preferred embodiment of the present invention the system is based on an array of sensors (channels), measuring sleep parameters in a sleeping subjects and in their environment. An adaptable controller integrates the inputs from the sensors in real time, and controls the environmental condition protocol in a dynamic manner via stimulation delivering devices. The stimulation level is continuously adjusted as not to awaken the sleeping subject, and is based upon algorithms of convergence toward a desired sleep pattern. The said convergence algorithms may be adjusted to individual variation, desired results, specific disorders and limitation. Such limitations may include restrictions imposed by other medical constraints. The algorithms also take into account the configurations and specifications of the monitoring and stimulation equipment.

Figure 1:
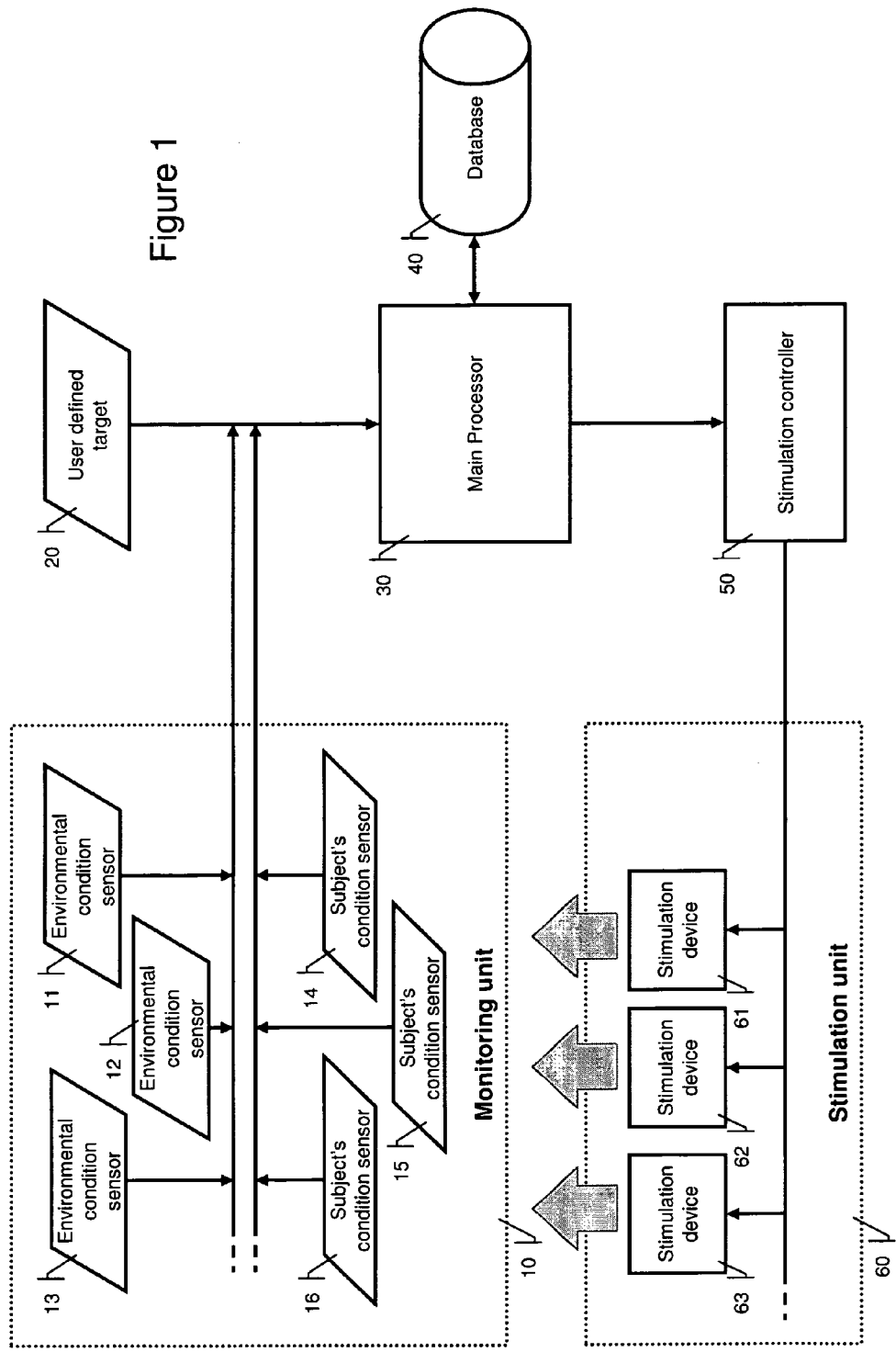
FIG. 1 is the operational cycle's flowchart according to preferred embodiments of the present invention.

FIG. 1 illustrates the operational cycle of the preferred embodiment of the present invention. The monitoring unit 10, which may be comprised of several environmental conditions sensors 11, 12, 13 and of several subject's condition sensors 14, 15, 16, sends data to the main processing unit 30. The main processing unit analyzes this data according to the user-defined desirable sleep architecture parameters 20 and the database information 40 and decides upon the next stage of the procedure. The decision is transferred to the stimulation controller which translates operation commands to the available stimulation devices 61, 62, 63. The changes caused by the stimulation devices 61, 62, 63 and other uncontrollable factors in the environment affect the readings of the monitoring unit's sensors 11-16. The monitoring unit 10 then transfers this new data to the main processor 30 and the cycle continues. The invention is not limited by the cycle rate, which can vary, depending upon the transfer rate from the monitoring unit 11-16 and the target of the protocol and can range from less then once every second to once every several hours (from 100 Hz to 0.0001 Hz). For example reasonable accurate identification of an apnea or an hypopnea event require operating in cycles of 10 Hz while for a rough estimation of REM phase a 0.01 Hz sampling is sufficient. Preliminary clinical studies suggest the need for addressing different compartments at different timescales. In addition, the sensory factors manipulated by the system vary in their changeability rates and in the timescale that takes for them to take effect. While changes in the audio or in the vibrating stimulators may happen rapidly and may cause changes in the subject's condition within seconds, changes in temperature take much longer to create and affect the subject's condition only several minutes later.

Figure 2:
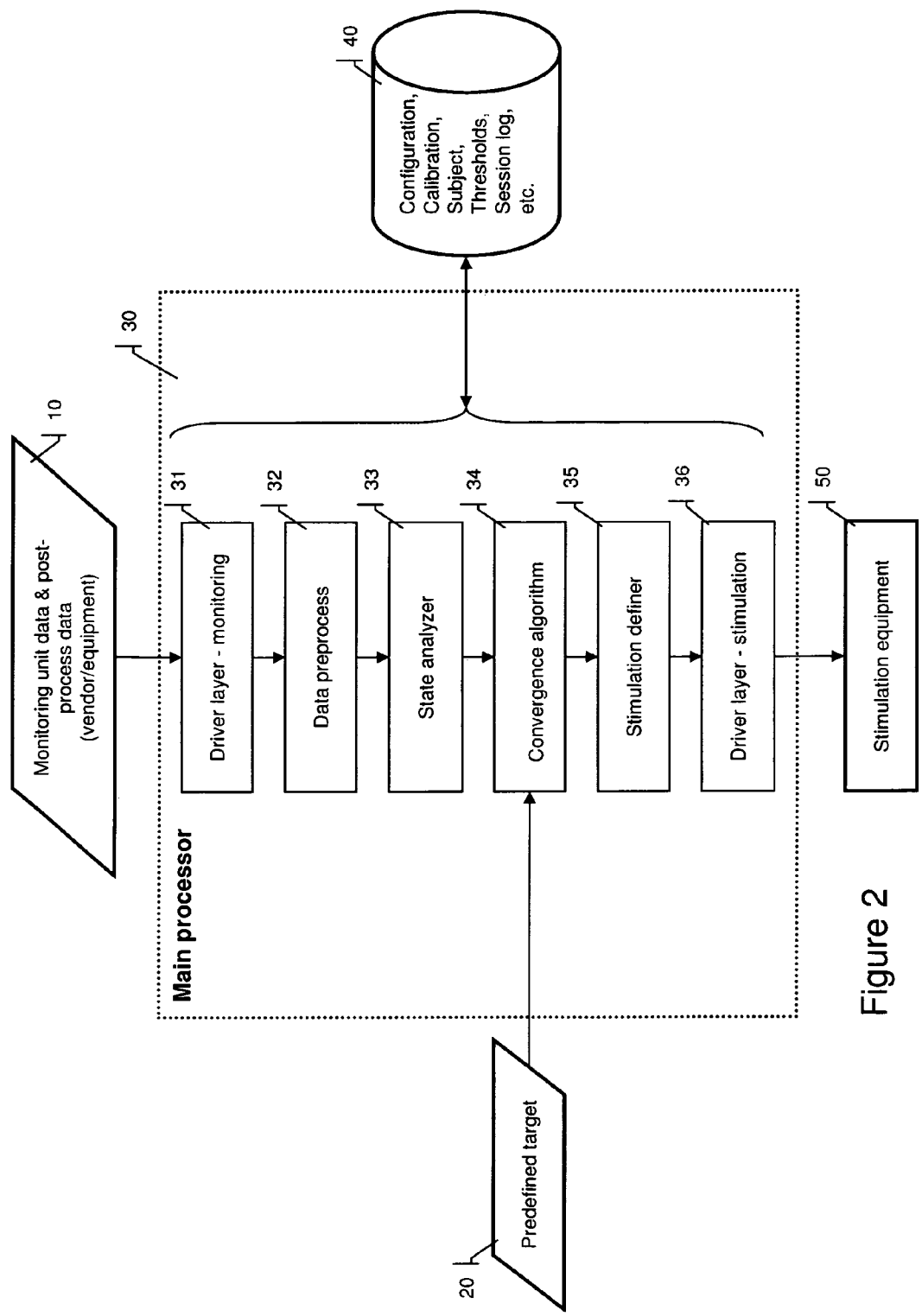
FIG. 2 is a block diagram of the logical structure of the main processor as specified in the present invention.

FIG. 2 is a block diagram of the logical structure of the main processor as specified in the present invention. The data from the monitoring unit 10 is first interpreted in the driver layer 31 (which is vendor\equipment dependent and may use vendor procedures), and is then further processed by a data preprocessor 32 (which analyzes frequency, morphology, artifacts, performs noise reduction, etc.) and translated to an abstract and uniform representation; then it is streamed into a 'state analyzer' module 33. The data from the state analyzer is analyzed by the 'convergence algorithm' module 34 (both modules are further described below) in comparison to the predefined target states 20 by retrieving the needed information from the system data bases 40. The needed changes in the environmental condition are then determined and streamed into the stimulation definer 35. The particular environmental stimulation is translated according to the configuration of the particular embodiment to operational commands which may be executed on the available equipment. These commands are then passed via a driver layer 36, preferably employing vendor procedure to the stimulation equipment 50. The system maintains and updates a set of data bases 40 holding the data needed for the different modules, including, for example, but not limited to, criteria for convergence, configuration data, hardware and software specifications, subject's specific thresholds and condition, the log of activities and any other essential data. The computational modules may be implemented as software on a personal computer, on dedicated hardware, manually activated by an operator or any combination of the methods.

The State analyzer is a component which receives data from the monitoring unit. This data may be received in a wide variety of channel specifications (including EEG, EMG, GSR and other), a wide variety of pre-processing degrees at the level of equipment (raw data, pre-processed, filtered data, integrated data from several channels, triggered by changes in the sleep stage or other) and in a wide variety of sampling rates and delays. All of these parameters are determined by specific embodiment; the scope of this invention is not limited by any of these data attributes. The state analyzer reads the specific configuration, in particular the configuration of the type of data inputted and level of processing of that data. In accordance with this information the state analyzer determines the state of the subject and other parameters of interest, concerning the subject or the environment. The state analyzer may, for example, need to determine the sleeping stage of the subject based on the frequency and morphology of specific channels, employing standard procedures from an EEG channel, it may receive data which is already processed and contains the current sleep stage (i.e. stages 1, 2, 3, 4 and REM) or only REM/NREM information. The state analyzer may also operate based on partial and incomplete data.

Convergence algorithm determines which of the stimulation needs to be applied, while the "stimulation regime deliverer" translates the stimulation into commands to the equipment supplying the stimulation via the output driver layer. The algorithms have local and global components implying that the stimulation protocol may be different for same given conditions, depending on the recorded sleeping patterns during the current night session. The logically construction of the convergence algorithms block is hierarchical, where at the top level the targeted results of the running session are situated. Such target results may include, for example, preventing apnea events or providing the subject with the best 3 hour sleep. At the lowest level are the specific stimulations to be delivered as a response to the current state as it is obtained from the state analyzer. The convergence algorithms block analyzes the current state and integrates it with data history (such as data from the beginning of the night, for example) as well as the night's desirable targets and other information (i.e. current time, patient sensitivity, internal translation tables and others). As a result of this analysis it initiates stimulation or perform changes the current stimulation. An illustrative example now follows. The predefined target for a subject is not to be allowed more then 20 minutes of REM sleep within a given cycle. After monitoring 15 minutes of the REM phase, a protocol for inducing a lighter sleep (stages 1 or 2) is initiated. The convergence algorithms block controls the protocol in soft real time, receiving data about the current state and about stimulations needed to induce lighter sleep while not causing arousal. If the desired effect is not achieved the convergence algorithm block may, for example, gradually increase the intensity of the stimulation, or initiate a different "stronger" protocol. Upon achieving the goal of lighter sleep the stimulation fades in a gentle way.

The system optionally includes a trace recording possibility (log file) able to record the acquired sleep and environmental parameters. This may serve as the basis for learning algorithms, thus allowing a post-processing analysis for enhancing the convergence algorithms, for ensuring treatment efficacy and for research purposes.

As mentioned above, the system initiates changes in the sleeping person's proximity, which may affect the person's sensory input. Any of the senses may receive stimulation in different facets; following is a description of exemplary stimulations manipulations in the subject's proximity. The system may be programmed to operate via one sensory pathway, or integrate the influence of several pathways.

The visual system may perceive stimulations in different degrees of intensity (luminescence), frequency (colour), pattern (for moving light), luminescence derivative (time between change in the luminescence level). However, depending on the lighting equipment available and the specific protocol, certain embodiments of the present invention may not employ all the components and the degrees of freedom. A simple embodiment may have control over the on/off switch of a light in the room. A more complex embodiment may employ a dimming device, and a full light feature embodiment may employ a live controlling protocol (for example DMX protocol) to activate LED based lighting devices or a light source with controllable filters. Another embodiment may make use of semi-transparent mattresses, blankets and pillows with internal light sources which may be controlled as stimulation units.

The audio parameters are intensity (volume), music and sound types, intensity derivative (time between change in the sound intensities) and the sound patterns, alternation and combination of kinds of sounds. For example Beethoven's $7^{th}$ symphony will cause different effect then Chopin's nocturnes. When using the present invention music will be chosen from a sound library stored in some magnetic or optic form, and controlled by the main controller.

Producing changes in environmental light and sound has proved to have an effect on sleeping subjects. Due to research it is now known that during sleep light in the environment is registered by the sleeping person by the eyes through the eyelids and sound via the ears. However, future research may find that light enters and is registered via other channels, for example via receptors in the skin or newly discovered photoreceptor pathways (Melanopsin or Cryptochromes or Phytochromes), and that sound can affect the system via other mechanisms, such as via internal frequency detector receptors. The scope of the invention is thus not limited to any particular receptive channel; its protocols may be updated in order to integrate any physiological mechanism that may be discovered characterized and proved to be biological relevant.

Mechanical vibrations at various intensity levels may be applied as a sensory stimulation path in a variety of places, such as the head, the neck or the higher and lower back. The vibration engines may be sited within the mattress. Preferably, to avoid adaptation, few small vibrating units should be placed at different locations. These vibrations are felt regardless of the person's position.

During sleep, fluctuations in the person's metabolism are reflected in the changes in body temperature. Both ambient and core temperature are well determined factors that are known to influence the sleep architecture. Certain embodiments of the present invention may include devices which affect the temperature in the proximity of the sleeping person in order to achieve specific changes in the body temperature. These changes may, for example, alter the time ratio between Rapid Eye Movement (REM) sleep and to Non-Rapid Eye Movement (NREM) sleep, or prolong the slow wave sleep (stages 3 and 4). The temperature control apparatus should preferably be close to the subject by employing commercially available controllable air-conditions or electrical mattress and blanket, for example.

Embodiments of the present invention may also include means for adjusting controllable equipment which is able to deliver, and preferably also remove specific aromas in the proximity of the sleeping person. In the same manner described in this section, other stimulation methods that will prove to be effective in modulating the sleeping architecture may be included in the scope of the present invention. Such stimulation may be, but are not limited to, means for generating fluctuations in the magnetic fields around the subject, producing mechanical vibrations and humidity, for example.

The preferred embodiments of the present invention are comprised of non-invasive and non-hazardous stimulation methods, applied in a gentile fashion, making subtle and gradual changes in the environment. The system provides the user with the means to fully preprogram the operation of the stimulation generating devices as well as control them in real time.

The system may also provides the user with preset stimulation protocols that is based on clinical experiments which were found to be affective for achieving desirable sleep architectures or for the treatment of specific disorders such as snoring, OSAS, Periodic Limb Movement (PLM), hypersomnia or insomnia, for example. General disorders which may be cured or improved at the level of cause or symptom by manipulating the sleep pattern may also be treated.

As mentioned before, there are several recognized, well calibrated and established method for providing indications about sleep components and their correlations. The overall integration of measurement of different physiological variables yields measurements data and scoring methods, of both the whole night sleep and the sleep architecture, which represent the dynamics of sleep. The monitored variables may vary from 32 channels (full scale polysomnograph) to 2 or even a single channel giving some indication as for the state of the sleeping subject. Depending on the quality, number of channels and analysis abilities of the monitoring and processing equipments, the results vary from data on each individual channels at 512 Hz to simple sleep stage tracking or just simply identifying the REM stage. The level of reliability of the recognition of these sleep states (all in the scope of the present invention) and sleep events are therefore not uniform in the different embodiments of the invention. The preferred embodiments make use of non-intrusive monitoring equipment, and employ remote monitoring. Methods for remote monitoring of the sleeping phases may include sleeping position analyzer, facial expression analyzer, or a wave detector of respirations, for example. These methods may require a one-time calibration process in order to study the sleeping habits of any specific subject, but once this process is completed, the operation of the system is simple and without disturbing the patient.

Different embodiments may be suited for different user needs. An embodiment which is composed of a full scale 32 channel monitoring apparatus, a device for fine-tuning multiple stimulation generators and a main processor with highly detailed analysis and processing abilities may suite a professional sleep laboratory, while an embodiment composed of a dual or a single channel monitoring apparatus, means for a partial control over a single or a couple of low cost stimulation generators, combined with a simple low cost processing unit may answer the need of everyday home use. Embodiments which combine simple and sophisticated equipment are also within the scope of the present invention, as well as embodiments which operate without monitoring equipment. The user interface of the different embodiments may also vary between highly complex professional interfaces to simple interfaces suited to be operated by untrained personnel.

An additional part of the invention is the setting up of a library of stimulation patterns designed for the treatment of certain disorder or disorders and for specific alteration in the sleep architecture, including stimulation patterns for falling asleep and waking up. For example in the case of light stimulation, applying green light upon entering phase 1, blue light upon entering phase 2, indigo upon entering phase 3 and violet upon entering phase 4, or progressively increasing the intensity of light as the desired time of awakening approaches. Further examples are applying a red light upon encountering an apnea event, or upon identification of a pattern leading to an apnea event, applying a full repetitive pattern of lights and sounds normalized to the time allowed for sleep, or applying a protocol of warm colors at stage 2 aimed at inducing a deep sleep.

The implementation of the system may comprise any commercially available technologies and components. However, certain embodiments of the present invention may require making use of specially designed equipment, in particular regarding real time control processor and stimulation generating equipment as in the case of aroma stimulation, light controlled semi-transparent pillows, facial expression analyzer may able to determine the subject's sleep stage and other sleep parameters and events, and so on.

One possible manner of making use of the present invention may include, for example, a pre-configuration stage at a sensory perception laboratory, where the individual parameters and sensitivities in relation to sensory stimulation and their effect are determined, thus allowing only minimal configuration changes at the patient's home. Alternatively the system may start operating employing predefined stimulations and automatically perform tuning and adaptations during operation.

The system may also facilitate the 'falling asleep' phase, by making use of certain light patterns and frequencies in varying intensities, by adjusting the temperature and by producing soothing sounds, for example. This is performed in accordance to the sleep-monitoring device toward reaching light sleep (stage one and two). Similarly, a 'waking up' protocol may be included, in which the subject is moderately projected into waking phase, instead of the shock awakening produced by an alarm clock, as is frequently the case. This application may be especially important for heart patients for whom the shock awakening might be hazardous.

There is a large variability sleeping habits among individuals who are not diagnosed as suffering from a chronic sleep related disorder. The variability may be found in any sleep related parameter, from overall time of sleep to its effectiveness, sleep architecture and patterns as well as state of alertness. Handling this variability and correcting it in order to improve the effectiveness of the sleep or change it toward certain goals is within the scopes of the present invention.

Adaptation of the established protocols within the framework of the system is envisioned as being useful during waking hours as well. For example, in addition to the regular lights, a light source and/or a sound source may continue to dynamically be adjusted in order to bring the subject to the desired state of alertness determined according to different criteria or presets.

An additional embodiment of the present invention may make use of the invention's basic structure for recording the level of noise and movement in a given public space and manipulating it according to the same principles of the invention. For example, in a management room, during a management meeting the level of light or the room temperature can be modulate in such a way as to prevent too loud noise (shouting) or too little (non-interest), without directly interfering with the activity in the room. The temperature may vary gradually say 1 to 3 degrees while the light may change in a range of 10%. Other examples include parties, waiting halls, conference halls, shopping malls, waiting rooms, train stations, class rooms and so on.

In this writing and the added figures, the details of calibration, logging, learning, general and specific configuration, error handling, thresholds, recovery procedures and so on are not mentioned but are part of embodiments of the invention.

The present invention is not restricted to human subjects, and applications in which the level of activity and state in vertebrates, for example, poultries or of a heard of sheep is dynamically manipulated. Moreover an application of the patent at a different timescale is envisioned in which plant growth, for example in a greenhouse, is manipulated. Furthermore, the invention may have embodiments in a fluid environment for controlling fish or alga daily cycles or growth patterns.

While the above description contains much specificity, these should not be construed as limitations on the scope of the invention, but rather as exemplification of the preferred embodiments. Those skilled in the art will envision other possible variations that are within its scope. Accordingly, the scope of the invention should be determined not only by the illustrated embodiments, but by the appended claims and their legal equivalents.

APPENDIX—APPLICATION EXAMPLES

Example 1

A subject has multiple sleep apneic events. Upon identifying an apneic event (or a pattern leading to it) the systems activates a light regimen. The light regimen is applied to induce a lighter sleep stage, 2 or 3, or trigger a sleep position change in the subject which is correlated with less apneic events. Upon setting the proper regime at the clinic, the subject is instructed to continue the treatment at home three nights a week. The set-up at home includes a simplified EEG and EOG, and a controllable light source applied for example in the room, or directly on the eye lid through LED (light emitting diode) based glasses. The predefined protocols configured and calibrated to the specific sleep environment are then applied according to the monitor's data.

Example 2

An adult sleep approximately nine hours on regular basis, and wishes to reduce the amount of sleeping hours without affecting the quality of sleep (amount of slow wave and REM). At home the subject uses a predefined protocol following a specific sequence of stimulations via one of the sensory stimulation pathways, such as light, for instance. The full protocol will last a certain amount of time (in our example 9 hours) that will progressively decrease. With time, the subject's system will adjust the sleep time without affecting deep stages of sleep. The subject, upon going to sleep, operates the system manually.

Example 3

In an intensive care unit (ICU), a patient may have access to a screen providing visual and audio stimulations that both promote and regulate the sleep pattern and architecture and assist in regulating the time orientation. As an example, a simple protocol will simulate on the screen the day/night luminescence patterns. "Sun-set" and "sun-rise" protocols may be employed by night shift workers upon going to sleep and awakening, respectively. The same protocols may be used by subjects suffering from jet-leg and wishing to quickly adjust to the new time zone.

Example 4

An audio pattern is set to end a prolonged REM state (according to predefined criteria), or a different audio pattern is set to bring the subject into slow wave sleep (stages 3 and 4). A different audio pattern is set to gradually wake the subject up. This pattern is automatically initiated at a given time before the expected awakening time.

Example 5

The subject works long hours in a monotonous, sleep promoting environment. A modified sleep monitoring system (consisting of EEG and motion channels only) is attached to the patients head recognizing sleep events and gently arouses the subject by applying a preset light pattern directly over the eyelids. The same application is employed, for example, for drivers or pilots who need to stay awake. The stimulation path and intensity are adjusted for the individual sensitivity (such as the subject's tolerance to sudden actions), the environment and the requirements of the job. Furthermore the intensity can be increased and the light pattern can be changed if the desired response is not detected by the monitoring unit.

What is claimed is:

1. A system for dynamically affecting sleep architecture and sleep states of a subject in soft real time for treating sleep disorders and improving sleep quality, said system comprising:

stimulation generators for applying stimulation over said subject; and monitoring means for measuring the subject's physiological and the environmental conditions, wherein activation of each stimulation is based upon an interactive session algorithm, operatively associated with said monitoring means, wherein said interactive session algorithm includes a state analyzing module for analyzing subject sleep state by measuring the subject's physiological conditions, and a convergence algorithm, operatively associated with said stimulation generators and monitoring means, wherein said convergence algorithm enables receiving the measured condition and sleep state of the subject and determining the stimulation to be activated and applied upon the subject, and wherein said convergence algorithm includes an iterative convergence process that is associated with at least one predefined target, wherein said process allows applying stimulations over the subject, receiving measurements of the subject's physiological condition and changing the applied stimulation according to the received measurements in relation to said target.

2. The system of claim 1 wherein the sleep disorder is at least one of the following: apnea, hypopnea, snoring.

3. The system of claim 1 further enabling to manipulate states of alertness and patterns of behavior.

4. The system of claim 3 wherein said alertness states include at least one of the following: sleepiness, drowsing driving, narcolepsy.

5. The system of claim 1 wherein the stimulation generators relate to light, sound, odor, temperature, magnetic fields, humidity, air composition and mechanical stimulations.

6. The system of claim 1 wherein the convergence module operation is based on stimulation protocols relating to specific conditions for achieving specific targets, wherein the said protocols can be configured and adapted to the respective stimulation equipment.

7. The systems of claim 1 wherein stimulation protocols are based on translation module between stimulation and expected effects in which the said algorithms can be configured and adapted to particular sensitivities and limitations in accordance with individual variability, including personal preference habits, adaptation and sensitization.

8. The system of claims 1 further comprising references profiles of disordered and or normal subjects wherein said references are used for analyzing subjects' condition and state for determining stimuli activation.

9. The system of claim 1 wherein the subjects are humans, as individuals or in groups.

10. The system of claim 1, wherein the subjects are animals as individuals or in groups.

11. The system of claim 1 wherein the subjects are plants as individuals or in groups.

12. The system of claim 1 wherein the environment in which the subject is located is fluid, as individuals or in groups.

13. The system of claim 1 wherein said algorithm further bases its decisions upon subject previous data measurements at earlier phases.

14. The system of claim 1 wherein state analyzing module further analyses user state and current measurements to estimate next state of the subject.

15. The system of claim 1 wherein the measurement data can be collected through different channel specifications.

16. The system of claim 1 further including analyzing means for processing historical data of the same subject and data from similar templates for improving the algorithm stimulation protocols and creating new protocols.

17. The system of claim 1 wherein the monitoring means include only internal clocks for triggering and activating the stimulation protocols.

18. The system of claim 1 wherein the monitoring means include manual means to be activated by an operator or the subject for triggering and activating the stimulation protocols.

19. A method for dynamically affecting sleep architecture and sleep state of a subject in soft real time for treating sleep disorders and improving sleep quality, said method comprising the steps of:

monitoring and measuring subject physiological conditions in real time;

measuring environmental conditions;

analyzing sleeping state of the subject according to measurement of the subject's physiological conditions;

determining stimulation activation parameters according to a convergence algorithm; and activating stimulation generators according to determined activation parameters, wherein said convergence algorithm includes an iterative convergence process that is associated with at least one predefined target, wherein said process allows applying stimulations over the subject, receiving measurements of the subject's physiological condition and changing the applied stimulation according to the received measurements in relation to said target.

20. The method of claim 19 wherein the sleep disorder is at least one of the following: apnea, hypopnea, snoring.

21. The method of claim 19 further enabling to manipulate states of alertness and patterns of behavior.

22. The method of claim 21 wherein said alertness states include at least one of the following: sleepiness, drowsing driving, narcolepsy.

23. The method of claim 19 wherein the stimulation generators relate to light, sound, odor, temperature, magnetic fields, humidity, air composition and mechanical stimulations.

24. The method of claim 19 wherein the convergence algorithm operation is based on stimulation protocols relating to specific conditions for achieving specific targets, wherein the said protocols can be configured and adapted to the respective stimulation equipment.

25. The method of claim 19 wherein the stimulation protocols are based on translation between stimulation and expected effects in accordance with particular sensitivities and limitations in accordance with individual variability, including personal preference and habits.

26. The method of claim 19 further comprising references profiles of disordered and or normal subjects wherein said references are used for analyzing subjects' condition and state for determining stimulus activation.

27. The method of claim 19 wherein the subjects are humans, as individuals or in groups.

28. The method of claims 19 wherein the subjects are animals, as individuals or in groups.

29. The method of claims 19 wherein the subjects are plants, as individuals or in groups.

30. The method of claims 19 wherein the environment in which the subject is located is fluid, as individuals or in groups.

31. The method of claim 19 wherein the convergence algorithm further bases its decisions upon subjects previous data measurements at earlier phases.

32. The method of claim 19 wherein the state analyzer algorithm further analyzes user state, log data of the present session and current measurements to estimate next subject state.

33. The method of claim 19 further including the step of analyzing and processing historical data for improving the algorithm stimulation protocols and creating new protocols.

34. The system of claim 1, wherein said convergence algorithm enables defining at least one of: at least one stimulation type to be applied: the intensity of the stimulation.

* * * * *